United States Patent
Higgins et al.

(10) Patent No.: US 7,873,397 B2
(45) Date of Patent: Jan. 18, 2011

(54) SPECTROSCOPIC OPTICAL SYSTEM

(76) Inventors: Richard Higgins, 5909 Cali Glen La., Westerville, OH (US) 43082; Betty Lise Anderson, 200 Glenhurst Ct., Gahanna, OH (US) 43230

( * ) Notice: Subject to any disclaimer, the term of this patent is extended or adjusted under 35 U.S.C. 154(b) by 385 days.

(21) Appl. No.: 11/765,231

(22) Filed: Jun. 19, 2007

(65) Prior Publication Data

US 2008/0316466 A1    Dec. 25, 2008

(51) Int. Cl.
*A61B 5/1455* (2006.01)
(52) U.S. Cl. .................. 600/316; 600/310; 600/473
(58) Field of Classification Search .......... 600/309, 600/310, 316, 322, 473
See application file for complete search history.

(56) References Cited

U.S. PATENT DOCUMENTS

| | | | |
|---|---|---|---|
| 7,643,860 B2 * | 1/2010 | Gueissaz | 600/310 |
| 2002/0026106 A1 * | 2/2002 | Khalil et al. | 600/310 |
| 2002/0082487 A1 * | 6/2002 | Kollias et al. | 600/316 |
| 2005/0148834 A1 * | 7/2005 | Hull et al. | 600/317 |
| 2005/0203358 A1 * | 9/2005 | Monfre et al. | 600/331 |
| 2006/0211927 A1 | 9/2006 | Acosta | |
| 2006/0276697 A1 * | 12/2006 | Demuth et al. | 600/322 |
| 2007/0049809 A1 * | 3/2007 | Bechtel et al. | 600/316 |

OTHER PUBLICATIONS

John L Smith, The Pursuit of Noninvasive Glucose: "Hunting the Deceitful Turkey," 2006.
Charlotte Eliasson, Anthony W. Parker, Allen E. Goodship, Edward R.C. Draper, Richard J. Swinburne, Ian P. Clark, Kate L. Ronayne, Mike Towrie, Neil MacLeod, Darren P. Andrews, Nicholas Stone, and Pavel Matousek, SORS—A Novel Method for Sub-Surface Raman Spectroscopy of Tissue and Powders, Poster, Publication date unknown but prior to Jun. 19, 2007.
P. Matousek, I. P. Clark, E. R. C. Draper, M. D. Morris, A. E. Goodship, N. Everall, M. Towrie, W. F. Finney, and A. W. Parker, Subsurface Probing in Diffusely Scattering Media Using Spatially Offset Raman Spectroscopy, Applied Spectroscopy, vol. 59, No. 4, 2005.

* cited by examiner

*Primary Examiner*—Eric F Winakur
(74) *Attorney, Agent, or Firm*—Steptoe & Johnson PLLC

(57) ABSTRACT

Innovative techniques that result in a better signal-to-noise ratio for spectrographic analysis of substances in a target than conventional techniques. In these techniques, light illuminates a target with at least some of the light penetrating the target. At least a portion of the light that penetrates the target is collected from a region on the target's surface that is not directly illuminated. Preferably, at least a majority of the collected light is light that penetrates the target. Also preferably, the light that illuminates the target is in a pattern that partially but not completely surrounds the region from which the portion of the light that penetrates the target is collected. A spectrum of at least a portion of the collected light is analyzed.

40 Claims, 5 Drawing Sheets

SPECTROSCOPIC OPTICAL SYSTEM

BACKGROUND OF THE INVENTION

1. Field of the Invention

This invention relates to a spectroscopic optical system, for example a system for Raman spectroscopy to measure a blood and/or tissue analyte such as glucose, cholesterol, collagen, β-Hydroxybutyrate or keratin.

2. Description of the Related Art

Blood analytes are typically measured by drawing a small amount of blood from a person and then analyzing that blood using any of numerous known techniques. For example, people suffering from diabetes usually draw a drop of blood several times a day in order to measure their glucose levels using a handheld glucose measuring device.

Because blood must be drawn, these typical techniques are invasive and inconvenient. As a result, only a limited number of samples typically are taken per day outside of hospitals and medical care facilities where blood can be drawn frequently or continuously.

Use of spectroscopy to measure blood and/or tissue analytes non-invasively has been proposed. In particular, Raman spectroscopy has been proposed as a technology that could permit frequent or even constant non-invasive measuring of blood analytes. U.S. Pat. No. 7,039,448, titled "Zero Corrected Optical Blood Analyte Detector," assigned to DIRAmed, LLC, discloses one technique for using a stable, naturally occurring tissue component such as cholesterol to calibrate a spectroscopic device for measuring a blood analyte. U.S. Pat. No. 7,039,448 is hereby incorporated by reference as if fully set forth herein.

Although techniques for measuring blood glucose in vivo using spectroscopy have been proposed, actual real-world implementation has proven to be very elusive. A book has even been written on the subject: *The Pursuit of Noninvasive Glucose: "Hunting the Deceitful Turkey"* by John L. Smith (copyright 2006).

SUMMARY OF THE INVENTION

One significant problem with using spectroscopy to measure a blood or tissue analyte is that conventional optical systems result in too low of a signal-to-noise ratio. As a result, more powerful and bulkier optical systems are required. These bulkier systems are not practical for widespread consumer use.

In more detail, spectroscopy involves illuminating a target and analyzing the spectrum of the light returning from the target. With conventional techniques, the light returning from the target includes two components: light that bounces off the target and light that slightly penetrates the target before returning from the target. In some forms of spectroscopy such as Raman spectroscopy, only the light coming back from slightly penetrating the target contains the spectrum of interest. The light that bounces off the target primarily represents noise. Unfortunately, in many settings, most of the light directed toward the target bounces off. Therefore, the signal-to-noise ratio tends to be high in these settings.

The invention addresses this problem with innovative techniques that result in a better signal-to-noise ratio for spectrographic analysis of substances in a target. In these techniques, light illuminates a target with at least some of the light penetrating the target. At least a portion of the light that penetrates the target is collected from a region on the target's surface that is not directly illuminated. Preferably, at least a majority of the collected light is light that penetrates the target. Also preferably, the light that illuminates the target is in a pattern that partially but not completely surrounds the region from which the portion of the light that penetrates the target is collected. A spectrum of at least a portion of the collected light is analyzed.

By virtue of the foregoing, at least a good portion of the collected and analyzed light is not light that has bounced off of the target's surface, but rather is light that has penetrated the target and then returned to a region on the target's surface that is not directly illuminated. As a result, the signal-to-noise ratio for the spectrum tends to be much better than that produced by conventional techniques.

In preferred embodiments, the light that illuminates the target is coherent monochromatic light from a laser or laser diode in a crescent-shaped, semi-circle-shaped, hyperbolic-shaped, or parabolic-shaped pattern. The pattern preferably is formed using only refractive, transmissive, or refractive and transmissive optics.

Other patterns besides a crescent-shaped, semi-circle-shaped, hyperbolic-shaped, or parabolic-shaped pattern can be used. Preferably, collection of the light is performed using collection optics directly in contact with the target. This tends to further reduce noise.

In one embodiment used to measure a person's glucose levels, the light is infrared with a wavelength in the range of 785 nanometers to 850 nanometers, the spectroscopy is Raman spectroscopy, and the target is the person's skin.

The invention encompasses methods and devices that utilize the foregoing techniques. Such methods and devices exhibit significantly improved signal-to-noise ratios over methods and devices that use conventional techniques. As a result, a consumer device for measuring blood glucose levels becomes commercially feasible.

While these methods and devices were designed in the context of using Raman spectroscopy to measure blood analytes, the improved signal-to-noise ratios can be advantageous for many other types of spectroscopy. These other types of spectroscopy include but are not limited to ex vivo (e.g., in a lab) Raman spectroscopy to measure substances in blood, to analyze pharmaceuticals, and to analyze other substances and materials, as well as non-Raman spectroscopy.

This brief summary has been provided so that the nature of the invention may be understood quickly. A more complete understanding of the invention may be obtained by reference to the following description of the preferred embodiments thereof in connection with the attached drawings.

DESCRIPTION OF THE PREFERRED EMBODIMENT

Briefly, light illuminates a target with at least some of the light penetrating the target. At least a portion of the light that penetrates the target is collected from a region on the target's Surface that is not directly illuminated. Preferably, at least a majority of the collected light is light that penetrates the target. Also preferably, the light that illuminates the target is in a pattern that partially but not completely surrounds the region from which the portion of the light that penetrates the target is collected. A spectrum of at least a portion of the collected light is analyzed.

By virtue of the foregoing, at least a good portion of the collected and analyzed light is not light that has bounced off of the target's surface, but rather is light that has penetrated the target and then returned to a region on the target's surface that is not directly illuminated. As a result, the signal-to-noise ratio for the spectrum tends to be much better than that produced by conventional techniques.

Figure 1:
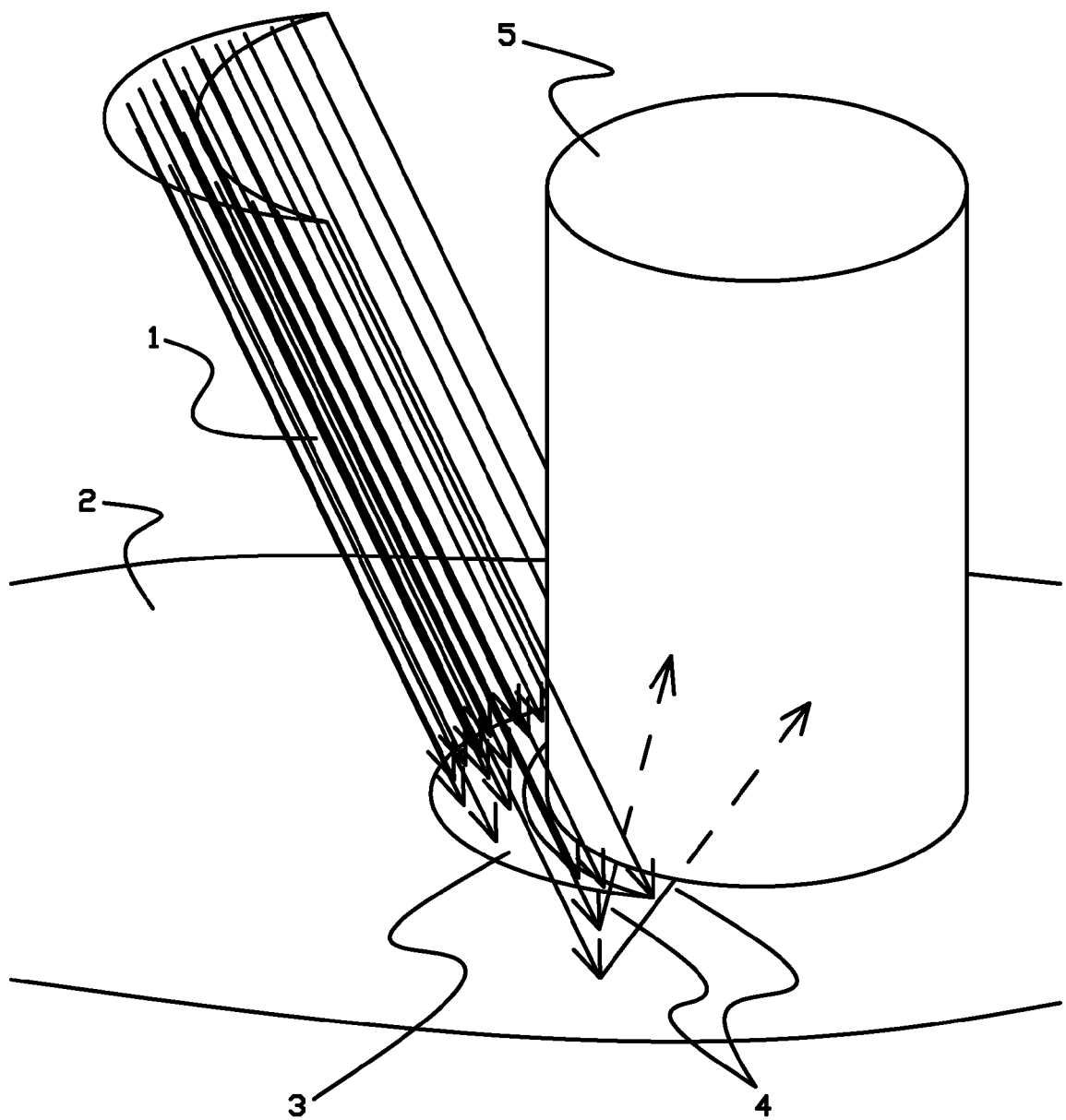
FIG. 1 shows a conceptualized view of spectroscopy according to the invention.

In more detail, FIG. 1 shows light 1 illuminating target 2 in pattern 3 on a surface of the target. At least some of the light penetrates the target, as illustrated by arrows 4. Some of this penetrating light interacts with atoms and/or molecules below the surface of target 2. At least a portion of this light then returns to the surface in a region that is not directly illuminated, that is outside of pattern 3. Collection optics 5 collects at least a portion of the light in that region. In order to help reduce noise, at least a majority of the light collected by collection optics 5 preferably is light that penetrates the target as opposed to light that bounces off the target and/or ambient light. A spectrum of at least a portion of the collected light is analyzed.

Figure 2:
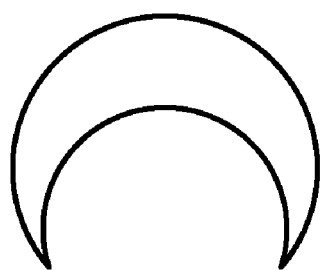
FIGS. 2 to 6 show examples of some light patterns that can be used for spectroscopy according to the invention.

In a preferred embodiment, pattern 3 of light 1 that illuminates target 2 partially but not completely surrounds a collection region from which the portion of the light that penetrates the target is collected. In FIG. 1, this pattern is a crescent-shaped light pattern. The crescent-shaped light pattern is shown more clearly in FIG. 2.

Figure 3:
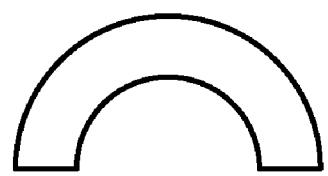
Figure 4:
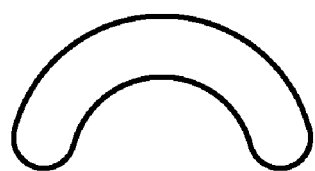
Figure 5:
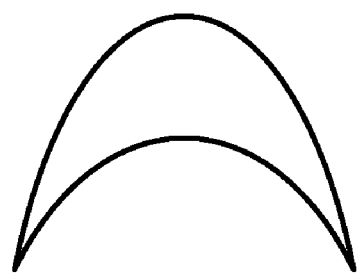
Figure 6:
Figure 6:
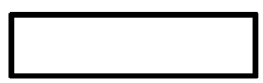

The invention is not limited to any particular light pattern. Rather, the illuminating light can have virtually any shaped pattern that partially but not completely surrounds the collection region. FIGS. 3 to 6 show some possible examples. FIGS. 3 and 4 show examples of semi-circle-shaped light patterns. FIG. 5 shows an example of a parabolic-shaped or half of a hyperbolic-shaped light pattern. FIG. 6 shows an example of a double rectangle-shaped light pattern. Other patterns can be used, for example but not limited to patterns that include crescent-shaped, semi-circle-shaped, circle-shaped, parabolic-shaped, hyperbolic-shaped, arc-shaped, curve-shaped, ellipse-shaped, line-shaped, rectangle-shaped, and/or square-shaped portions or segments.

Even though virtually any shaped light pattern that partially but not completely surrounds the collection region can be used, curved patterns with an open concave side are preferred. These patterns tend to be easily generated. Furthermore, simple collection optics can be placed near the open concave side of the light pattern, with the collection optics close to a significant portion of the light pattern while not actually being directly illuminated by the light pattern. This is preferred because direct illumination of the collection optics could both waste illuminating light and be a source of additional noise for any spectrographic analysis.

Light from a light source preferably is formed into the light pattern using only refractive, transmissive, or refractive and transmissive optics. Masking optics are not preferred because they result in a significant loss of light, which in turn can necessitate a more powerful and therefore bulkier light source. In addition, diffraction issues can arise from light passing an edge of a mask, which can complicate any spectrographic analysis. A diffractive grating such as a hologram also can be used to form the light pattern, but this also is not preferred because of inefficiencies inherent in diffraction gratings. Nonetheless, masking, diffractive, and other types of optics can be used if so desired.

Light 1 preferably is coherent monochromatic light, for example from a laser or laser diode. Use of coherent monochromatic light tends to improve the accuracy of analysis of the spectrum. The light can be collimated, converging, or diverging.

As noted above, at least a majority of the light collected by collection optics 5 preferably is light that penetrates the target as opposed to light that bounces off the target and/or ambient light. To this end, the collection optics preferably are placed directly in contact with the target or at least significantly close to the target (e.g., within a few millimeters).

The foregoing technique can be used in conjunction with Raman spectroscopy to measure glucose content in vivo of one or more of tissue, interstitial fluid, and blood in a person's skin. In an embodiment designed to do this, light 1 preferably is infrared with a wavelength in the range of 785 nanometers to 850 nanometers, and target 2 is the person's skin.

Embodiments of the invention as described above for measuring glucose content in vivo preferably should satisfy the following design parameters:

Efficiently illuminate skin with light from an excitation laser or laser diode. This preferably includes efficient coupling of light energy to the skin.

Distribute the light in such a manner that (1) tissue damage is prevented and (2) an area and pattern of illumination on the skin is at a controlled distance away from a desired collection region.

Maximize collection efficiency of optics to capture Raman photons emanating from (beneath a surface of) the skin as a result of illumination through efficient coupling.

Maximize transmission efficiency of both input and output optics to minimize laser or laser diode power requirements needed for accurate signal detection and analysis.

Minimize spectral noise from both the input optical train and output optical train to provide maximum signal-to-noise ratio.

While embodiments that meet these goals are preferred, the invention is in no way limited to implementations and embodiments that satisfy all or even some of these goals.

FIGS. 7 to 10 show various embodiments of optical systems that can be used to perform spectroscopy according to the invention. The invention is not limited to these optical systems.

Figure 7:
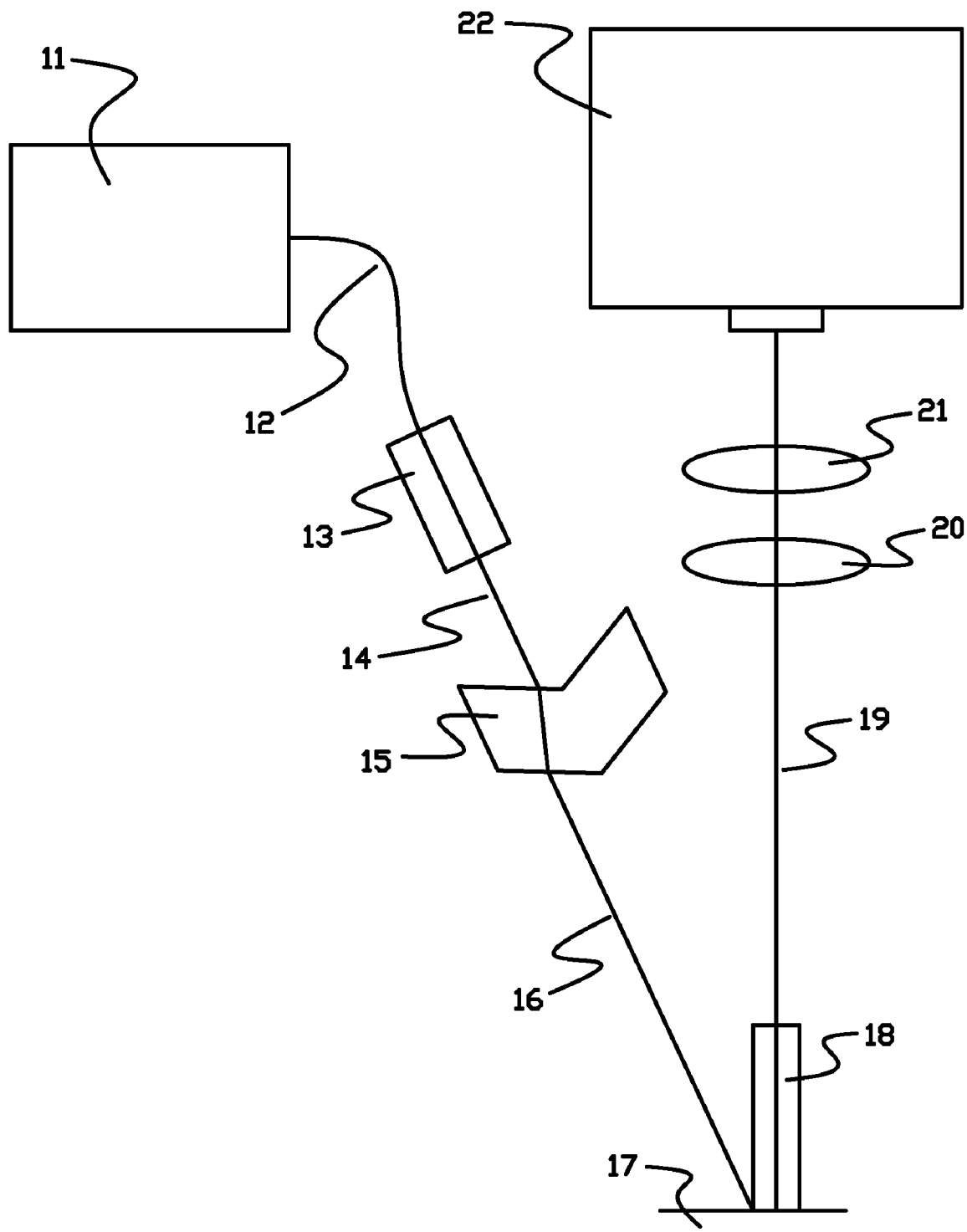
FIGS. 7 to 10 show various embodiments of optical systems that can be used to perform spectroscopy according to the invention.

In FIG. 7, laser 11 is coupled to fiber optic patch cord 12, which in turn is coupled to fiber collimator 13. The arrangement results in solid excitation light beam 14. The excitation light beam strikes off-axis concave-convex axicon 15, resulting in crescent-shaped excitation light beam 16 shaped along the lines of the pattern shown in FIG. 2. The crescent-shaped excitation light beam strikes target 17. At least a portion of the excitation light beam penetrates the target. Some of the excitation light beam that penetrates the target interacts with atoms and/or molecules in the target and then returns out of the target. Collection optics in the form of light pipe 18 collects at least a portion of this returning light, which forms collection light beam 19. The collection light beam is imaged and/or conditioned by lenses 20 and 21 and analyzed by spectrometer 22.

In one implementation of the embodiment shown in FIG. 7, various of the elements have the following characteristics and/or specifications:

Laser 11: 785 nm-850 nm 350 mW gas or solid state laser
Fiber optic patch cord 12: 100/125 um diameter
Fiber collimator 13: Thorlabs ADI IF collimator
Solid excitation beam 14: ~2 mm diameter
Concave-convex axicon 15:
Convex surface angle=140°
Concave surface angle=140°

Diameter=12.7 mm
Edge thickness=11 mm
Material=PMMA
Alignment:
  Angular: parallel to optical axis
  Lateral: 1 mm from optical axis in the direction toward light pipe 18
  Distance from laser=unimportant
Light pipe 18:
2.0 mm diameter core
Cladding: 0.1 mm thick, 100 mm long
Lens 20: Newport PN 77799
Lens 21: Newport PN 40550
BSC PCX 1.5" diameter
75 mm focal length
Spectrometer 22:
Raman spectrometer—Newport PN 78129
Near infrared (200 cm$^{-1}$ to 1800 cm$^{-1}$)

Neither the embodiment shown in FIG. 7 nor the invention is limited to these specific characteristics and/or specifications.

Figure 8:
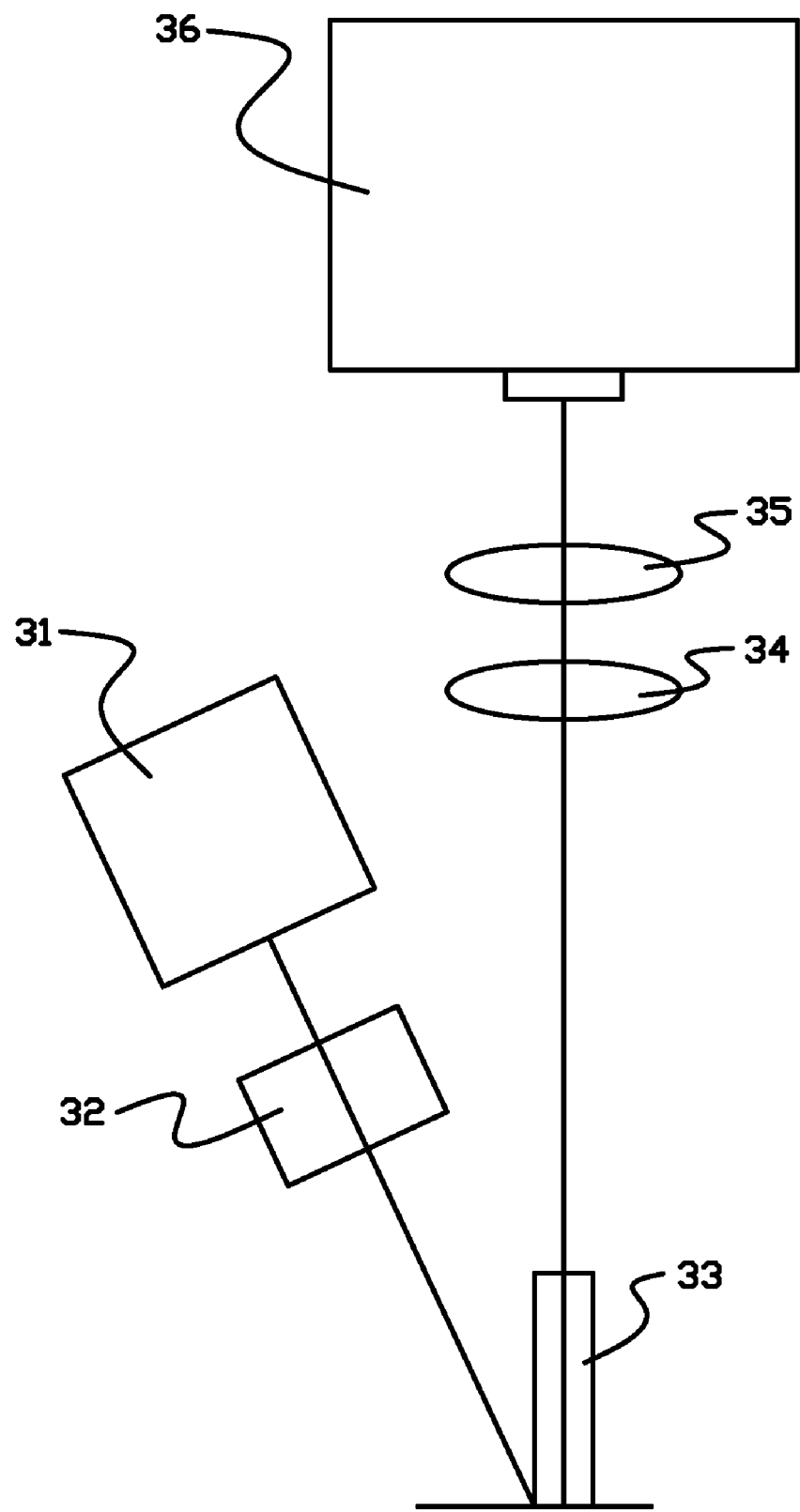

FIG. 8 shows another embodiment that utilizes a laser diode instead of a laser. In FIG. 8, laser diode 31 generates diverging elliptical light beam 32. Beam-shaping optics 33 shape the light beam into an appropriate shape. For example, beam-shaping optics 33 could be an aspheric-offset concave axicon, resulting in a divergent crescent-shaped excitation light beam. The collecting optics 34, shaping and/or conditioning lenses 35 (optional), and spectrometer 36 can be any suitable collecting optics, lenses and spectrometer, including but not limited to those described above with respect to FIG. 7.

Figure 9:
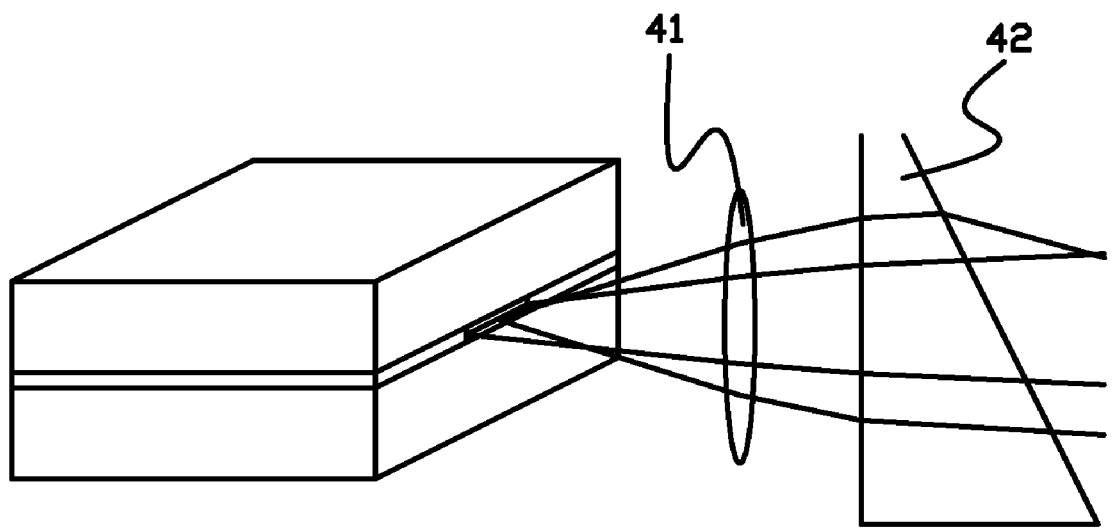
Figure 10:
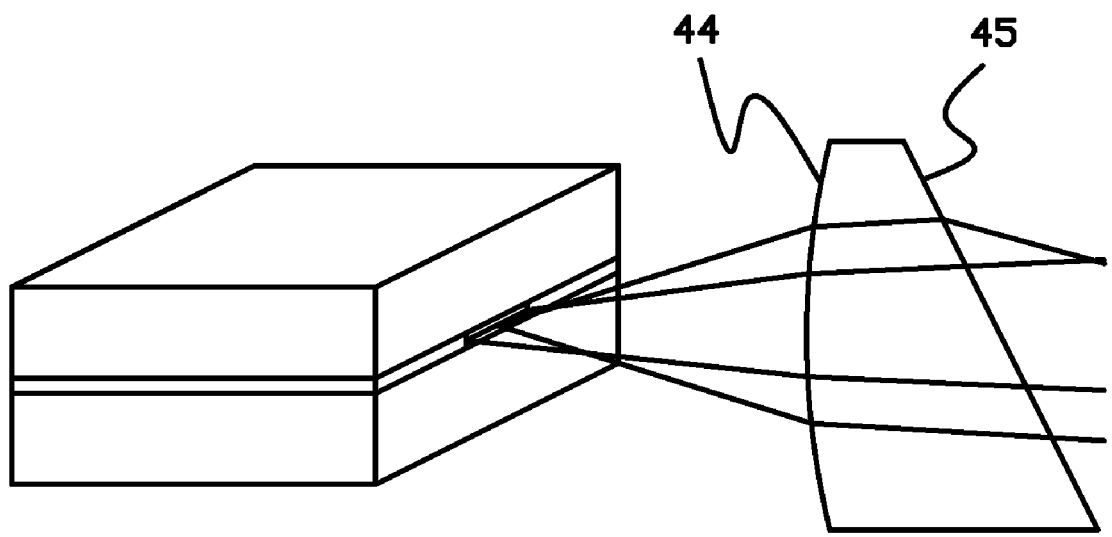

FIGS. 9 and 10 show examples of beam-shaping optics 33 that can be used in the embodiment of FIG. 8. In FIG. 9, the beam-shaping optics include fast axis aspheric collimating lens 41 and plano-concave axicon 42. In FIG. 10, the beam-shaping optics include a custom lens having convex aspheric surface 44 and offset concave axicon surface 45. In both of these examples, the beam-shaping optics result in a light pattern for the excitation beam along the lines of that shown in FIG. 3.

Due to its relative simplicity and scale, the embodiment shown in FIG. 10 is particularly well suited for use in a handheld consumer device for measuring a person's glucose levels.

While the foregoing methods, devices, and techniques were designed in the context of using Raman spectroscopy to measure blood and/or tissue analytes, the improved signal-to-noise ratios can be advantageous for many other types of spectroscopy. These other types of spectroscopy include but are not limited to ex vivo (e.g., in a lab) Raman spectroscopy to measure substances in blood, to analyze pharmaceuticals, and to analyze other substances and materials, as well as non-Raman spectroscopy. The invention encompasses use of the foregoing methods, devices, and techniques with such other types of spectroscopy.

ALTERNATIVE EMBODIMENTS

The invention is in no way limited to the specifics of any particular embodiments and examples disclosed herein. For example, the terms "preferably," "preferred embodiment," "one embodiment," "this embodiment," and the like denote features that are preferable but not essential to include in embodiments of the invention. The terms "comprising" or "including" mean that other elements and/or steps can be added without departing from the invention. Many other variations are possible which remain within the content, scope and spirit of the invention, and these variations would become clear to those skilled in the art after perusal of this application.

What is claimed is:

1. A method of performing Raman spectroscopy, comprising the steps of:
  illuminating a target with light from a light source, with at least some of the light penetrating the target;
  collecting, with collection optics, at least a portion of the light that penetrates the target from a region on the target's surface not directly illuminated by the step of illuminating, wherein at least a majority of the light collected by the step of collecting is light that penetrates the target;
  analyzing, with Raman spectroscopic instrumentation, a spectrum of at least a portion of the light collected by the step of collecting; and
  wherein the light that illuminates the target is in a pattern that partially but not completely surrounds the region from which the portion of the light that penetrates the target is collected.

2. A method as in claim 1, wherein the light that illuminates the target is in a crescent-shaped, semi-circle-shaped, hyperbolic-shaped, or parabolic-shaped pattern.

3. A method as in claim 2, wherein the crescent-shaped, semi-circle-shaped, hyperbolic-shaped, or parabolic-shaped pattern is formed using only refractive, transmissive, or refractive and transmissive optics.

4. A method as in claim 2, wherein the crescent-shaped, semi-circle-shaped, hyperbolic-shaped, or parabolic-shaped pattern is formed using one of more of refractive, transmissive, masking, or diffractive optics.

5. A method as in claim 1, wherein the step of collecting the light is performed using collection optics directly in contact with the target.

6. A method as in claim 1, wherein the light that illuminates the target comprises coherent monochromatic light.

7. A method as in claim 6, wherein the coherent monochromatic light is from a laser or laser diode.

8. A method as in claim 1, wherein the light comprises infrared light.

9. A method as in claim 8, wherein the infrared light has a wavelength in the range of 785 nanometers to 850 nanometers.

10. A method as in claim 1, wherein the target comprises a person's skin.

11. A method as in claim 10, wherein the spectrum of light is measured to determine a glucose content of one or more of tissue, interstitial fluid, and blood in the person's skin.

12. A method of performing Raman spectroscopy, comprising the steps of:
  illuminating a target with light from a light source, with at least some of the light penetrating the target;
  collecting, with collection optics, at least a portion of the light that penetrates the target from a region on the target's surface not directly illuminated by the step of illuminating;
  analyzing, with Raman spectroscopic equipment, a spectrum of at least a portion of the light collected by the step of collecting; and
  wherein the light that illuminates the target is in a pattern that partially but not completely surrounds the region from which the portion of the light that penetrates the target is collected.

13. A method as in claim 12, wherein the light that illuminates the target is in a crescent-shaped, semi-circle-shaped, hyperbolic-shaped, or parabolic-shaped pattern.

14. A method as in claim 13, wherein the crescent-shaped, semi-circle-shaped, hyperbolic-shaped, or parabolic-shaped pattern is formed using only refractive, transmissive, or refractive and transmissive optics.

15. A method as in claim 13, wherein the crescent-shaped, semi-circle-shaped, hyperbolic-shaped, or parabolic-shaped pattern is formed using one or more of refractive, transmissive, masking, or diffractive optics.

16. A method as in claim 12, wherein the step of collecting the light is performed using collection optics directly in contact with the target.

17. A method as in claim 12, wherein the light that illuminates the target comprises coherent monochromatic light.

18. A method as in claim 17, wherein the coherent monochromatic light is from a laser or laser diode.

19. A method as in claim 12, wherein the light comprises infrared light.

20. A method as in claim 19, wherein the infrared light has a wavelength in the range of 785 nanometers to 850 nanometers.

21. A method as in claim 12, wherein the target comprises a person's skin.

22. A method as in claim 21, wherein the spectrum of light is measured to determine a glucose content of one or more of tissue, interstitial fluid, and blood in the person's skin.

23. A device that performs Raman spectroscopy, comprising:
   a light source configured to illuminate a target with light, with at least some of the light penetrating the target;
   collection optics configured to collect at least a portion of the light that penetrates the target from a region on the target's surface not directly illuminated by the light source, wherein at least a majority of the light collected by the collection optics is light that penetrates the target;
   Raman spectrographic instrumentation that analyzes a spectrum of at least a portion of the light collected by the collection optics; and
   wherein the light that illuminates the target is in a pattern that partially but not completely surrounds the region from which the portion of the light that penetrates the target is collected.

24. A device as in claim 23, further comprising beam shaping optics that form the light that illuminates the target into a crescent-shaped, semi-circle-shaped, hyperbolic-shaped, or parabolic-shaped pattern.

25. A device as in claim 24, wherein the beam shaping optics comprise only refractive, transmissive, or refractive and transmissive optics.

26. A device as in claim 24, wherein the beam shaping optics comprise one or more refractive, transmissive, masking, or diffractive optics.

27. A device as in claim 23, wherein the collection optics are adapted to be directly in contact with the target.

28. A device as in claim 23, wherein the light that illuminates the target comprises coherent monochromatic light.

29. A device as in claim 28, wherein the light source comprises a laser or laser diode.

30. A device as in claim 23, wherein the light comprises infrared light.

31. A device as in claim 30, wherein the infrared light has a wavelength in the range of 785 nanometers to 850 nanometers.

32. A device that performs spectroscopy, comprising:
   a light source configured to illuminate a target with light, with at least some of the light penetrating the target;
   collection optics configured to collect at least a portion of the light that penetrates the target from a region on the target's surface not directly illuminated by the light source;
   Raman spectrographic instrumentation that analyzes a spectrum of at least a portion of the light collected by the collection optics; and
   wherein the light that illuminates the target is in a pattern that partially but not completely surrounds the region from which the collection optics collect the portion of the light that penetrates the target.

33. A device as in claim 32, further compromising beam shaping optics that form the light that illuminates the target into a crescent-shaped, semi-circle-shaped, hyperbolic-shaped, or parabolic-shaped pattern.

34. A device as in claim 33, wherein the beam shaping optics comprise only refractive, transmissive, or refractive and transmissive optics.

35. A device as in claim 33, wherein the beam shaping optics comprise one or more of refractive, transmissive, masking, or diffractive optics.

36. A device as in claim 32, wherein the collection optics are adapted to be directly in contact with the target.

37. A device as in claim 32, wherein the light that illuminates the target comprises coherent monochromatic light.

38. A device as in claim 37, wherein the light source comprises a laser or laser diode.

39. A device as in claim 32, wherein the light comprises infrared light.

40. A device as in claim 39, wherein the infrared light has a wavelength in the range of 785 nanometers to 850 nanometers.

* * * * *